United States Patent [19]

Morawietz et al.

[11] Patent Number: 6,121,499
[45] Date of Patent: Sep. 19, 2000

[54] PROCESS FOR PRODUCING POLYHYDROXY ETHERS AND UNSYMMETRICAL POLYHYDROXY ETHERS OBTAINABLE WITH THE PROCESS

[75] Inventors: Marcus Morawietz, Hanau, Germany; Dietrich Arntz, Mobile, Ala.; Mathias Höpp, Biebergemünd, Germany

[73] Assignee: Degussa Aktiengesellschaft, Frankfurt, Germany

[21] Appl. No.: 09/033,896

[22] Filed: Mar. 3, 1998

[30] Foreign Application Priority Data

Mar. 4, 1997 [DE] Germany ............ 197 08 695

[51] Int. Cl.$^7$ .................. C07C 41/00; C07C 43/00
[52] U.S. Cl. .................. 568/579; 568/678; 568/679; 568/680
[58] Field of Search .................. 568/579, 678, 568/679, 680

[56] References Cited

U.S. PATENT DOCUMENTS 5,840,994  11/1998  Ninomiya et al. ............ 568/580

FOREIGN PATENT DOCUMENTS

0799815A1  10/1997  European Pat. Off. .

OTHER PUBLICATIONS

Chemical Abstract 100:51078, XP 002070582, Dec. 19, 1977, CS 197741 B, Feb. 28, 1983.
Chemical Abstract 79–115120, XP 002070583, Jun. 22, 1973, SU 387959, Jun. 22, 1973.
Chemical Abstract 93:72341, XP 002070584, 1979, Petrochemia (1979) 19 (6), 198–206.

Primary Examiner—Kathleen K. Fonda
Attorney, Agent, or Firm—Smith, Gambrell & Russell, LLP; Beveridge, DeGrandi, Weilacher & Young

[57] ABSTRACT

A process for producing polyhydroxy ethers having the formula (I) $(HO)_{(w-M)}W(OV)_m$, in which W represents an organic group and OV a structural element containing hydroxyl groups, having the formula (III)

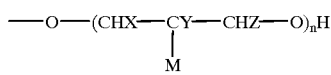

A multifunctional alcohol $W(OH)_w$ (II) is reacted with an α,β-unsaturated carbonyl compound $XCH{=}CY{-}CZ{=}O$ (IV) and formaldehyde in the presence of a base. The α,β-unsaturated carbonyl compound (IV) and the remaining quantities of formaldehyde, multifunctional alcohol (II) and base are added continuously or periodically to an aqueous solution or suspension containing at least 10 mole % of the multifunctional alcohol (II), at least 10 to 70 mole % of the formaldehyde and at least 10 mole % of the base. Preferred multifunctional alcohols (II) are pentaerythritol, TMP and TME. Preferred carbonyl compounds (IV) are acrolein and α-alkylacrolein. New asymmetric polyhydroxy ethers are also disclosed.

21 Claims, No Drawings

PROCESS FOR PRODUCING POLYHYDROXY ETHERS AND UNSYMMETRICAL POLYHYDROXY ETHERS OBTAINABLE WITH THE PROCESS

INTRODUCTION AND BACKGROUND

The present invention concerns a process for producing polyhydroxy ethers and the unsymmetrical polyhydroxy ethers obtainable with the process. The process is based on the reaction of a multifunctional alcohol with an $\alpha,\beta$-unsaturated aldehyde or ketone and formaldehyde in the presence of an alkali hydroxide or alkaline earth hydroxide under conditions for the aldol/Cannizzaro reaction.

Polyhydroxy ethers of the di-, tri-, and polypentaerythritol type having the general formula:

$$(HOCH_2)_3\text{---}C\text{---}O\text{---}[CH_2OH)_2CH_2\text{---}O]_nH$$

and corresponding polyhydroxy ethers based on trimethylolethane (TME) and trimethylolpropane (TMP) are becoming increasingly important as raw materials for special resins, lubricants, PVC stabilizers and PVC plasticizers. As polyhydroxy ethers of the above type have previously appeared only as small proportions of byproducts from the production of pentaerythritol, TME or TMP from acetaldehyde, propionaldehyde, or butyraldehyde, respectively, and formaldehyde form the combined aldol/Cannizzaro reaction, there has been no shortage of attempts to produce such polyhydroxy ethers as a goal (see, for instance, U.S. Pat. Nos. 2,325,589 and 2,490,567).

The yield of dipentaerythritol as a byproduct in the production of pentaerythritol can be increased somewhat, according to Japanese Patent Application 8 176 048 by using acrolein in place of part of the acetaldehyde. In this process, acetaldehyde and, if desired, part of the acrolein are put into an aqueous medium, and formaldehyde and acrolein are added dropwise, with the reaction being carried out at 0° to 50° C. in the presence of an alkali hydroxide. The yield of dipenta, based on acetaldehyde, was reported as 21 to 26%. According to the comparison example described in this process—reaction of pentaerythritol with acrolein and formaldehyde at 70° C.—dipentaerythritol was obtained in a yield of 8.5%, along with polymers of acrolein.

Czechoslovak Patent 197 741 describes a process for producing dipentaerythritol by reaction of pentaerythritol with acrolein and formaldehyde at 0° to 50° C., at a molar ratio of pentaerythritol to acrolein of 0.2 to 3 and a molar ratio of formaldehyde to acrolein of 1 to 10. The entire amount of formaldehyde is placed in the reaction vessel, and acrolein is added. Pentaerythritol is added at the beginning of or during the reaction. In the recovery steps of the process, only a very small yield of dipentaerythritol was obtained instead of the high yield stated in the patent; see Comparison Example 1 herein below.

Soviet Union Patent 387 959 teaches a process similar to that of the Czechoslovak patent. In this patent, 0.1 to 2 moles of pentaerythritol are used per mole of acrolein and the reaction is done with formaldehyde at 50° to 90° C. The molar ratio of acrolein to formaldehyde to alkali hydroxide is 1:3 to 7:0.25 to 2. Pentaerythritol and water are placed in the reaction vessel, and acrolein and formaldehyde are added dropwise. In the recovery step of this process, too, the yields found for dipentaerythritol and tripentaerythritol, and the total yield, were substantially lower than as stated in the patent; see Comparison Example 2 herein below.

It is, then, an object of this invention to obtain dipentaerythritol in higher yields, using the process principle presented for dipentaerythritol, for example.

According to another object, the invention should also make it possible to produce the nonsymmetric polyhydroxy ethers, which were not known previously.

SUMMARY OF THE INVENTION

The above and other objects of the invention can be achieved by a process for producing polyhydroxy ethers having the formula (I)

$$(HO)_{(w-m)}W(OV)_m \qquad (I)$$

in which W represents an organic group and OV represents a structural element containing a hydroxyl group, w is the functionality of a multifunctional alcohol having the formula:

$$W(OH)_w \qquad (II)$$

m is an integer between 1 and w, and OV is selected from structural elements having the general formula (III)

$$\text{---}O\text{---}(CHX\text{---}\underset{M}{\overset{|}{C}Y}\text{---}CHZ\text{---}O)_nH \qquad (III)$$

in which
X: is H, $C_1$ to $C_6$ alkyl, aryl, alkoxymethyl, aryloxymethyl;
Y: is H, $C_1$ to $C_6$ alkyl, aryl, alkoxymethyl, aryloxymethyl, carbalkoxymethyl, carbamidomethyl, or M;
Z: is H, $C_1$ to $C_6$ alkyl, aryl or X—Z taken together is a $C_2$ or $C_3$ alkylene group;
M: is —$CH_2OH$ or $$\text{---}CH_2\text{---}O\text{---}(CHX\text{---}\underset{CH_2OH}{\overset{|}{C}Y}\text{---}CHZ\text{---}O)_{n'}H$$

n, n': are integers from 1 to 5; and in which the alkyl and aryl in X, Y and Z may also be substituted and the m structural elements OV in the polyhydroxy ether (I) may be the same or different.

The process comprises reacting a multifunctional alcohol having the formula $W(OH)_w$ (II) with an $\alpha,\beta$-unsaturated carbonyl compound having the formula $$XCH{=}CY\text{---}CZ{=}O \qquad (IV)$$

in which X, Y and Z have the meanings stated above, except that Y is not M, and with formaldehyde in the presence of an alkali hydroxide or alkaline earth hydroxide in the aqueous phase at a pH above 7 and a temperature in the range of 0° to 100° C. In this reaction, the molar ratio of II to IV is 0.05 to 20, the molar ratio of formaldehyde to IV is 2 to 15 and the molar ratio of metal hydroxide equivalent to IV is 1–3.

The resulting reaction mixture is the acidified and the reaction products can be isolated.

It is a feature of the process of this invention that the $\alpha,\beta$-unsaturated carbonyl compound (IV) and the remaining formaldehyde, the remaining multifunctional alcohol (II) and the remaining alkali hydroxide or alkaline earth hydroxide are added continuously or periodically to an aqueous solution or suspension comprising at least 10 mole % of the multifunctional alcohol (II), at least 10 to 70 mole % of the formaldehyde and at least 10 mole % of the alkali hydroxide or alkaline earth hydroxide so that the formaldehyde in the reaction mixture is always in excess with respect to the α,β-unsaturated aldehyde or ketone (IV).

DETAILED DESCRIPTION OF THE INVENTION

An important feature of the invention is that the reaction system already contains part of the formaldehyde required for the reaction before addition of the α,β-unsaturated aldehyde or ketone (IV). That measure avoids polymerization of the α,β-unsaturated carbonyl compound, besides which the polyhydroxy ether can be obtained in higher yields that was possible with the previously known process.

The multifunctional alcohol used, having the formula $(HO)_wW$, in which w is an integer from 2 to about 1000, can be a monomer, oligomer or polymer, and can contain primary and/or secondary hydroxyl groups. The organic group W, which can have aliphatic, olefinic, and/or cycloaliphatic structural features, can also have, aside from at least two hydroxyl groups, other functional groups, such as groups of the series —O—, —COOMe (salts), —COOR, —SO$_3$Me (salts), —SO$_3$R, —PO$_3$Me$_2$, —NR$_2$, Halogen, CN, —S(O)—, or —SO$_2$—, in which R stands for alkyl and Me stands for an alkali metal or ammonium ion.

Of aliphatic or cycloaliphatic monomeric alcohols (II), one can, for example, use difunctional, trifunctional, tetrafunctional, pentafunctional and hexafunctional alcohols, such as those from the series ethylene glycol (EG), 1,2- and 1,3-propylene glycol (1,2-PD and 1,3-PD), butane-1,4-diol (1,4-BD), hexane-1,6-diol (1,6-HD), neopentyl glycol (NPG), 2-methyl-1,3-propanediol (2-methyl-1,3-PD), 2,2,4-trimethyl-1,3-pentanediol, 1,4- and 1,2-cyclohexanediol, tartaric acid, diethanolamine, oxaheptanediol, cyclohexane-1,4-dimethanol, dimethylolacetic acid, glycerol, trimethylolethane (TME), trimethylolpropane (TMP), trimethylolacetic acid, diglycerol, pentaerythritol (penta), Di-TME, Di-TMP (=2,6-bis(hydroxymethyl)-2,6-diethyl-4-oxa-1,6-heptanediol), dipentaerythritol (dipenta=2,2,6,6-tetrakis(hydroxymethyl)-4-oxa-1,6-heptanediol), triglycerol, tripentaerythritol (tripenta), Tri-TMP, Tri-TME, monosaccharides and disaccharides. Particularly preferred monomeric alcohols (II) are those with 2 to 6 primary hydroxy groups. The polymeric compounds of Formula II include, for instance, polyvinyl alcohol, starches, polysaccharides, and poly(meth)acrylates and copolymers thereof, containing as the monomeric unit a hydroxyalkyl (meth)acrylate.

The α,β-unsaturated carbonyl compound (IV) to be used according to the invention can be an aldehyde or a ketone. Aldehydes, that is, compounds (IV) with Z being H, are preferred. Groups X and Y in (IV) can also have substituents that are stable under the reaction conditions, such as —N—alkyl$_2$, —N—aryl$_2$, —CO(O)alkyl, —OC(O)aryl, —COO—alkyl, —COO—aryl, or —CON—alkyl$_2$. While X and Y in compound IV can have the meanings previously stated, especially H, C$_1$ to C$_4$—alkyl and aryl, compounds with X and preferably also Y identical to H are preferred. Examples of α,β-unsaturated ketones include vinyl-alkyl ketones, such as vinylmethyl ketone, and vinyl-aryl ketones, such as vinylphenyl ketone. Examples of α,β-unsaturated aldehydes (IV) include: acrolein, methacrolein, 2-ethylacrolein, 2-n-propyl-, 2-n-butyl- and 2-isobutylacrolein; 2-arylacroleins such as 2-phenylacrolein, 2-p-tolylacrolein, and 2-p-hydroxyphenylacrolein; 2-alkoxymethylacroleins such as 2-methoxymethylacrolein; and 2-aryloxymethylacroleins such as 2-phenoxymethylacrolein.

A difunctional to hexafunctional alcohol (II) with primary hydroxyl groups and an α,β-unsaturated aldehyde (IV) in which X is equal to H and Y is equal to H or C$_1$- to C$_4$-alkyl or phenyl are preferred for the reaction.

The reaction principle, as shown in the diagram below makes it possible to produce symmetrical and unsymmetrical polyhydroxy ethers. While symmetric products are known, the unsymmetric products having Formula I are new compounds.

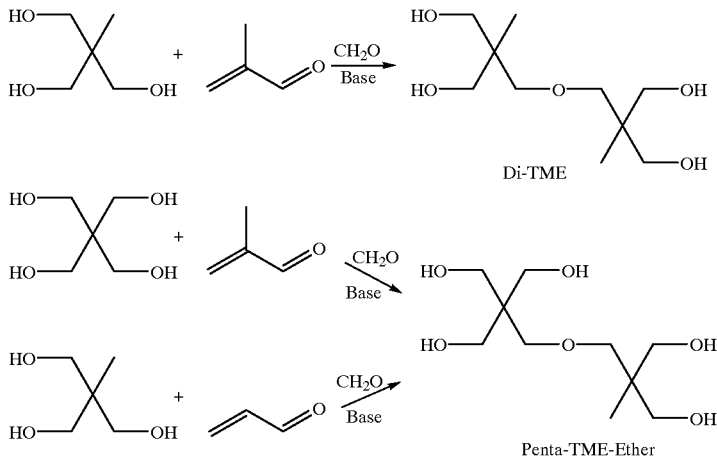

While the principal byproducts in the previously known process of the Soviet Union Patent 387 959 are tri- and poly-pentaerythritols, selectivity for dipentaerythritol is much higher in the process according to the invention. The pentaerythritol formed can be recycled.

Formaldehyde for the aldol condensation, and as the reducing agent in the Cannizzaro reaction can be used in any available form such as in suspension or solution, preferably as an aqueous solution containing 15 to 60% by weight, especially 15 to 30% by weight. While the initial reaction mixture must contain at least 10 mole % of the required formaldehyde, it is advisable for it to contain up to 50 mole %, preferably 20 to 50 mole %, and especially preferably 20 to 30 mole %, with the remainder added along with the α,β-unsaturated carbonyl compound.

This addition can be done continuously or periodically. In general, the molar ratio of formaldehyde to the α,β-unsaturated carbonyl compound (IV) is at least 2 to 1 when Y is not H, and at least 3 to 1 if Y is equal to H. Formaldehyde can even be used in great excess, up to about 15 to 1. After the end of the reaction, formaldehyde remaining can be separated from the reaction mixture either by steam distillation or by pressure distillation.

The multifunctional alcohol can be used as an aqueous solution or an aqueous suspension. It is advisable to have from 50 to 100 mole % of the alcohol in the initial reaction mixture, with the remainder added continuously or in portions during the addition of the α,β-unsaturated carbonyl compound. It can be a solution or suspension, or as a solid or liquid.

The molar ratio of multifunctional alcohol to α,β-unsaturated carbonyl compound depends on the structure of the polyhydroxy ether I to be prepared, on the degree of oligomerization, n and n', in structural element III, and on the value of M. For multifunctional alcohols II with 2 to 6 hydroxyl groups, the α,β-unsaturated carbonyl compound IV is usually used at a molar ratio for II to IV of 5 to 0.2.

The catalyst for the Cannizzaro reaction is a base, generally an alkali hydroxide or alkaline earth hydroxide, such as NaOH, KOH and $Ca(OH)_2$. The molar ratio of metal hydroxide equivalents to α,β-unsaturated carbonyl compound is preferably between 1 to 1 and 3 to 1. All the catalyst can be in the initial mixture, or part can be added during the reaction. Preferably 50 to 100 mole percent of the catalyst is placed in the aqueous solution or suspension.

The initial mixture contains water. The molar ratio of water to α,β-unsaturated carbonyl compound is preferably between 10 to 1 and 300 to 1, and in particular between 20 to 1 and 150 to 1.

The α,β-unsaturated carbonyl compound, the remaining formaldehyde and the catalyst can be added to the reaction vessel simultaneously or in succession. The raw materials can be premixed or added separately. However, an adequate excess of formaldehyde must be maintained in the reaction vessel.

The period over which the formaldehyde, the polyhydroxy compound and the α,β-unsaturated carbonyl compound are added is usually between 0.1 and 5 hours, typically between 0.5 and 3 hours. After the raw materials have been added, the reaction usually continues for up to 4 hours.

The process according to the invention is carried out at temperatures in the range of 0° to 100° C., and preferably in the range of 20° to 60° C. The reaction can be carried out at constant, rising, or falling temperature. In the phase following addition of the raw materials the mixture is stirred at 20° to 70° C., preferably 30° to 60° C.

The pH is maintained at 7 to 14, and especially 10 to 14, during the reaction. It has been found advantageous for optimal yield of polyhydroxy ethers to dissolve 100 mole % of the polyhydroxy compound of, for example, 2 to 6 hydroxy groups and 10 to 30% of the formaldehyde completely in water together with 100% of the catalyst, and to add the remaining 70 to 90% of the formaldehyde and the α,β-unsaturated carbonyl compound continuously, in parallel or premixed. The reaction time, or the addition time, is 1 to 3 hours and the reaction temperature is 30° to 60° C.

The reaction is followed by neutralization to convert the base into a salt. Formic acid is particularly suitable for neutralizing.

In the further processing, any formaldehyde still present is removed from the reaction mixture by distillation, as by pressure distillation or steam distillation. The polyhydroxy ether is separated from the metal formate ions produced by crystallization and then fractionally crystallized.

Differently structured polyhydroxy ethers can be produced according to the invention. The following list shows examples of unsymmetric polyhydroxy ethers produced according to the invention, with different carbon skeletons for W and the monomer unit of OV, by use of acrolein (a), methacrolein (b) and ethylacrolein (c). Such unsymmetric polyhydroxy ethers expand the possibilities for producing secondary products with specific properties from the groups of resins, lubricating oils, PVC stabilizers and plasticizers. One advantage of lubricating oils based on the unsymmetric polyhydroxy ethers is their lower congealing point. Also, the unsymmetric polyhydroxy ethers are more soluble than the symmetric ones. Polyhydroxy ethers according to the invention, based on a polymer containing hydroxyl groups, such as products of reaction of starches with acrolein and formaldehyde, are suitable as cobuilders and superabsorbents.

a) Polyhydroxy ethers (I) based on acrolein:
Penta-TME ether, penta-TMP ether, penta-di-TME ether, penta-di-TMP ether, penta-glycerol ether, penta-NPG ether, penta-1,2-Pd ether, penta-1,3-PD ether, penta-EG ether, penta-2-methyl-1,3-PD ether, penta-1,4-BD ether, penta-1,6-HD ether, penta-1,4-cyclohexanedimethanol ether, penta-2,2,4-trimethyl-1,3-pentanediol ether, penta-saccharide ether, penta-polysaccharide ether, bis(penta)-di-TME ether, bis(penta)-di-TMP ether, bis(penta)-TME ether, bis(penta)-TMP ether, bis(penta)-glycerol ether, bis(penta)-NPG ether, bis(penta)-1,2-PD ether, bis(penta)-1,3-PD ether, bis(penta)-EG ether, bis(penta)-2-methyl-1,3-PD ether, bis(penta)-1,4-BD ether, bis(penta)-1,6-HD ether, bis(penta)-1,4-cyclohexanedimethanol ether, bis(penta)-2,2,4-trimethyl-1,3-pentanediol ether, bis(penta)-saccharide ether, bis(penta)-polysaccharide ether tris(penta)-di-TME ether, tris(penta)-di-TMP ether, tris(penta)-TME ether, tris(penta)-TMP ether, tris(penta)-glycerol ether, tris(penta)-saccharide ether, tris(penta)-polysaccharide ether, tetrakis(penta)-di-TME ether, tetrakis(penta)-di-TMP ether, tetrakis(penta)-saccharide ether, tris(penta)-polysaccharide ether.

poly(penta)-saccharide ether b) Polyhydroxy ethers (I) based on methacrolein:
TME-tripenta ether, TME-dipenta ether, TME-di-TMP ether, TME-TMP ether, TME-glycerol ether, TME-NPG ether, TME-1,2-PD ether, TME-1,3-PD ether, TME-EG ether, TME-2-methyl-1,3-PD ether, TME-1,4-BD ether, TME-1,6-HD ether, TME-1,4-cyclohexanedimethanol ether, TME-2,2,4-trimethyl-1,3-pentanediol ether, TME-saccharide ether, TME-polysaccharide ether, bis(TME)-tripenta ether, bis(TME)-dipenta ether, bis(TME)-di-TMP ether, bis(TME)-penta ether, bis(TME)-TMP ether, bis(TME)-glycerol ether, bis(TME)-NPG ether, bis(TME)-1,2-PD ether, bis(TME)-1,3-PD ether, bis(TME)-EG ether, bis(TME)-2-methyl-1,3-PD ether, bis(TME)-1,4-BD ether, bis(TME)-1,6-HD ether, bis(TME)-1,4-cyclohexanedimethanol ether, bis(TME)-2,2,4-trimethyl-1,3-pentanediol ether, bis(TME)-saccharide ether, bis(TME)-polysaccharide ether, tris(TME)-tripenta ether, tris(TME)-dipenta ether, tris(TME)-di-TMP ether, tris(TME)-penta ether, tris(TME)-

TMP ether, tris(TME)-glycerol ether, tris(TME)-saccharide ether, tris(TME)-polysaccharide ether, tetrakis(TME)-tripenta ether, tetrakis(TME)-dipenta ether, tetrakis(TME)-di-TMP ether, tetrakis(TME)-penta ether, tetrakis-TME-saccharide ether, tetrakis(TME)-polysaccharide ether, pentakis(TME)-tripenta ether, pentakis(TME)-dipenta ether, pentakis(TME)-polysaccharide ether, hexakis(TME)-tripenta ether, pentakis(TME)-dipenta ether, pentakis(TME)-polysaccharide ether, heptakis(TME)-tripenta ether, hexakis(TME)-polysaccharide ether, octakis(TME)-tripenta ether, octakis(TME)-polysaccharide ether, poly(TME)-polysaccharide ether.

c) Polyhydroxy ethers (I) based on ethyl acrolein:

TMP-tripenta ether, TMP-dipenta ether, TMP-di-TME ether, TMP-glycerol ether, TMP-NPG ether, TMP-1,2-PD ether, TMP-1,3-PD ether, TMP-EG ether, TMP-2-methyl-1,3-PD ether, TMP-1,4-BD ether, TMP-1,6-HD ether, TMP-1,4-cyclohexanedimethanol ether, TMP-2,2,4-trimethyl-1,3-pentanediol ether, TMP-saccharide ether, TMP-polysaccharide ether, bis(TMP)-tripenta ether, bis(TMP)-dipenta ether, bis(TMP)-di-TME ether, bis(TMP)-penta ether, bis(TMP)-TME ether, bis(TMP)-glycerol ether, bis(TMP)-NPG ether, bis(TMP)-1,2-PD ether, bis(TMP)-1,3-PD ether, bis(TMP)-EG ether, bis(TMP)-2-methyl-1,3-PD ether, bis(TMP)-1,4-BD ether, bis(TMP)-1,6-HD ether, bis(TMP)-1,4-cyclohexanedimethanol ether, bis(TMP)-2,2,4-trimethyl-1,3-pentanediol ether, bis(TMP)-saccharide ether, bis(TMP)-polysaccharide ether, tris(TMP)-tripenta ether, tris(TMP)-dipenta ether, tris (TMP)-di-TME ether, tris(TMP)-penta ether, tris(TMP)-TME ether, tris(TMP)-glycerol ether, tris(TMP)-saccharide ether, tris(TMP)-polysaccharide ether, tetrakis(TMP)-tripenta ether, tetrakis(TMP)-dipenta ether, tetrakis(TMP)-di-TME ether, tetrakis(TMP)-penta ether, tetrakis-TMP-saccharide ether, tetrakis(TMP)-polysaccharide ether, pentakis(TMP)-tripenta ether, pentakis(TMP)-dipenta ether, pentakis(TMP)-polysaccharide ether, hexakis(TMP)-tripenta ether, hexakis(TMP)-dipenta ether, hexakis(TMP)-polysaccharide ether, heptakis(TMP)-tripenta ether, hexakis(TMP)-polysaccharide ether, octakis(TMP)-tripenta ether, octakis(TMP)-polysaccharide ether, poly(TMP)-polysaccharide ether.

The invention is further explained by the following of examples of the invention as well as comparison examples.

COMPARISON EXAMPLE 1

Production of dipentaerythritol according to Example 1 of Czechoslovak Patent 197741.

870 g water, 48 g (1.2 moles) NaOH, 140 g (1.03 mole) pentaerythritol and 400 g (4.0 moles) of aqueous 30% formaldehyde solution are placed in a flask at 40° C. 196.9 g of an aqueous 30% acrolein solution was added dropwise over a period of 15 minutes at that temperature. After addition of the acrolein, the reaction mixture was stirred for 30 minutes at 40° C. and then acidified to pH 6 with formic acid. The remaining formaldehyde was removed by steam distillation. The formaldehyde-free solution was evaporated completely and the dry residue was analyzed by gas chromatography.

| | |
|---|---|
| Residue from evaporation: | 365.1 g |
| Sodium formate: | 81.6 g |
| Organic compounds: | 283.5 g |

The following analytical balance and yield refers to the carbonyl component used, in this case, acrolein. It is the basis for all further experimental evaluations.

| Polyol | Composition of the residue (g) | Composition of the residue % | Yield based on acrolein (%) | Yield according to CS 197742 (%) |
|---|---|---|---|---|
| Pefo | 2.02 | 7.4 | 0.5 | not stated |
| Penta | 56.07 | 204.7 | — | — |
| Penta (new)* | — | 64.7 | 47.5 | 2.9 |
| Dipenta | 5.04 | 18.4 | 14.5 | 61.9 |
| Pe$_2$fo | 3.94 | 14.4 | 10.1 | not stated |
| Tripenta | 0.85 | 3.1 | 2.5 | 17.1 |
| Tetrapenta | 0.33 | 1.2 | 1.0 | not stated |
| Total yield | 68.25 | 249.2 | 76.1 | 81.9 |

*Penta (new): (penta in the reaction product) − (penta in the initial reaction mixture)
[k. A.:] Not stated
Pefo: pentaerythritol monoformal, 5,5-bis(hydroxymethyl)-1,3-dioxane
Pe$_2$fo: *bis(pentaerythritol) formal, 2,2,8,8-tetrakis(hydroxymethyl)-4,6-dioxanonane-1,9-diol

COMPARISON EXAMPLE 2

Production of dipentaerythritol according to Soviet Union Patent 387 959

272 g (2 moles) pentaerythritol and 350 g (19.4 mol) water were maintained at 70° C. in a 6-liter reaction vessel. 116 g (2 moles) acrolein (96%), 2250 g (9 moles) of 12% formaldehyde solution, and 168 g (3 moles) potassium hydroxide were added continuously and in parallel to that solution within 15 minutes at a constant temperature of 70° C. The reaction mixture became reddish during the reaction. After the addition, the reaction mixture was stirred for another 10 minutes at 70° C. Then the reaction mixture was adjusted to pH 6 with formic acid. The formaldehyde was removed by steam distillation and the composition of the reaction solution was analyzed by gas chromatography. The residue after evaporation weighed 730 g. The table shows the composition and yields:

| Polyol | Composition of the residue (%) | Composition of the residue (g) | Yield based on acrolein (%) | Yield according to SU 387 959 (%) |
|---|---|---|---|---|
| Pefo | 0.22 | 1.6 | 0.5 | not stated |
| Penta | 37.56 | 274.2 | — | — |
| Penta (new)* | — | 2.2 | 0.8 | 2.9 |
| | 13.06 | 95.3 | 37.5 | 41.8 |
| Dipenta | 0.58 | 4.3 | 1.5 | not stated |

-continued

| Polyol | Composition of the residue (%) | | Yield based on acrolein (%) | Yield according to SU 387 959 (%) |
|---|---|---|---|---|
| | (%) | (g) | (%) | (%) |
| Pe$_2$fo | 7.53 | 54.9 | 22.1 | 51.0 |
| Tripenta | 1.61 | 11.8 | 4.8 | not stated |
| Tetrapenta | | | | |
| Total yield | 60.56 | 442.1 | 67.2 | 95.7 |

*See footnote to Comparison Example 1

EXAMPLE 1
Production of Dipentaerythritol 545.6 g (4 moles) aqueous 22% formaldehyde solution, 272 g (2 moles) pentaerythritol, 3200 g (177 moles) water, and 96 g (2.4 moles) sodium hydroxide were maintained at 20° C. in a 6-liter reaction vessel. Over a period of 15 minutes, 116 g (2 moles) acrolein (96%) and 545.6 g (4 moles) 22% formaldehyde solution were added dropwise, continuously and in parallel, to the reaction vessel at a constant temperature of 20° C. Then 272.2 g (2 moles) 22% formaldehyde solution at 20° C. was warmed to 50° C. in 30 minutes and stirred for 30 minutes at that temperature. Then the pH of the solution was brought to 6 by adding formic acid and then the composition of the reaction solution was analyzed by gas chromatography. The residue after evaporation weighed 694 g. The table shows the composition and yields:

| Polyol | Composition of the residue (g) | Yield, based on acrolein (%) |
|---|---|---|
| Pefo | 2.7 | 0.9 |
| Penta | 363.5 | — |
| Penta (new)* | 91.5 | 33.6 |
| Dipenta | 102.0 | 40.1 |
| Pe$_2$Fo | 13.36 | 4.7 |
| Tripenta | 24.3 | 9.8 |
| Tetrapenta | 3.7 | 1.5 |
| Total yield | 509.6 | 90.6 |

*Penta (new): (penta in the reaction product) - (penta in the initial reaction mixture)

EXAMPLE 2
Production of Dipentaerythritol 272.8 g (2 moles) aqueous 22% formaldehyde solution, 272 g (2 moles) pentaerythritol, 3200 g (177 moles) water, and 96 g (2.4 moles) sodium hydroxide were maintained at 40° C. in a 6-liter reaction vessel. A premixed solution of 116 g (2 moles) acrolein (96%) and 1091.2 g (8 moles) 22% formaldehyde solution was added continuously over a period of 1 hour at a constant temperature of 40° C. After the addition, the reaction mixture was stirred for another 30 minutes at that temperature, and finally adjusted to pH 6 with formic acid. The formaldehyde was removed by steam distillation and the composition of the reaction solution was determined by gas chromatography. The residue on evaporation weighed 701 g. The composition and yields are shown in the table:

| Polyol | Composition of the residue (g) | Yield, based on acrolein (%) |
|---|---|---|
| Pefo | 1.5 | 0.5 |
| Penta | 348.8 | — |
| Penta (new)* | 76.8 | 28.2 |
| Dipenta | 119.8 | 47.1 |
| Pe$_2$fo | 2.8 | 1.0 |
| Tripenta | 37.2 | 15.0 |
| Tetrapenta | 8.6 | 3.5 |
| Total yield | 518.7 | 95.3 |

*See the footnote to Example 1

EXAMPLE 3
Production of Dipentaerythritol

The reaction was done as in Example 2, except that the reaction temperature was 50° C. and the acrolein and formaldehyde solution addition was done within 1 hour. The residue after evaporation was 699 g. The table show the composition and yields:

| Polyol | Composition of the residue (g) | Yield, based on acrolein (%) |
|---|---|---|
| Pefo | 1.5 | 0.5 |
| Penta | 350.4 | — |
| Penta (new)* | 78.4 | 28.8 |
| Dipenta | 124.8 | 49.1 |
| Pe$_2$fo | 2.3 | 0.8 |
| Tripenta | 31.0 | 12.5 |
| Tetrapenta | 8.0 | 3.3 |
| Total yield | 518.1 | 95.0 |

*See the footnote to Example 1

EXAMPLE 4
Production of Dipentaerythritol

The reaction was done as in Example 2, except that 93.6 g (1.2 moles) lime was used instead of the sodium hydroxide. The residue on evaporation weighed 715 g. The table shows the composition and yields.

| Polyol | Composition of the residue (g) | Yield, based on acrolein (%) |
|---|---|---|
| Pefo | 2.1 | 0.7 |
| Penta | 346.9 | — |
| Penta (new)* | 74.9 | 27.5 |
| Dipenta | 121.8 | 47.9 |
| Pe$_2$fo | 8.8 | 3.1 |
| Tripenta | 35.0 | 14.1 |
| Tetrapenta | 6.4 | 2.6 |
| Total yield | 521.0 | 95.9 |

*See Footnote to Example 1

EXAMPLE 5
Production of Dipentaerythritol

The reaction was carried out as in Example 3, except that 544 g (4 moles) pentaerythritol was used. The residue after evaporation weighed 965 g. Its composition and the yields are shown in the table:

| Polyol | Composition of the residue (g) | Yield, based on acrolein (%) |
|---|---|---|
| Pefo | 1.2 | 0.4 |
| Penta | 576.9 | — |
| Penta (new)* | 32.9 | 12.1 |
| Dipenta | 149.8 | 58.9 |
| Pe$_2$fo | 11.37 | 4.0 |
| Tripenta | 29.5 | 11.9 |
| Tetrapenta | 6.3 | 2.6 |
| Total yield | 775.1 | 89.9 |

*See Footnote to Example 1

EXAMPLE 6
Production of Dipentaerythritol

The reaction was done as in Example 3, except that 680 g (5 moles) pentaerythritol was used. The residue after evaporation weighed 1100 g. The table shows the composition and yields:

| Polyol | Composition of the residue (g) | Yield, based on acrolein (%) |
|---|---|---|
| Pefo | 0.6 | 0.2 |
| Penta | 692.8 | — |
| Penta (new)* | 12.8 | 4.7 |
| Dipenta | 170.6 | 67.1 |
| Pe$_2$fo | 6.8 | 2.4 |
| Tripenta | 41.9 | 16.9 |
| Tetrapenta | 11.3 | 4.6 |
| Total yield | 924.0 | 95.9 |

*See Footnote to Example 1

EXAMPLE 7

Production of dipentaerythritol, in which half the quantity of penta was in the initial reaction mixture and the other half was added during the reaction.

272.8 g (2 moles) aqueous 22% formaldehyde solution, 136 g (1 mole) pentaerythritol, 1600 g (88 moles) water and 96 g (2.4 moles) sodium hydroxide were maintained at 40° C. in a 6-liter reaction vessel. 116 g (2 moles) acrolein (96%) and 1091.2 g (8 moles) 22% formaldehyde solution were added continuously to this solution over a period of 2 hours at a constant temperature of 40° C. Simultaneously, 136 g (1 mole) pentaerythritol in 1600 g (88 moles) water was added continuously over a period of 1 hour. After the addition the reaction mixture was stirred for another 30 minutes at that temperature and then adjusted to pH 6 with formic acid. The formaldehyde was removed by steam distillation and the composition of the reaction solution was analyzed by gas chromatography. The residue after evaporation weighed 690 g. The table shows the composition and yields:

| Polyol | Composition of the residue (g) | Yield, based on acrolein (%) |
|---|---|---|
| Pefo | 2.8 | 1.0 |
| Penta | 367.8 | — |
| Penta (new)* | 95.8 | 35.2 |
| Dipenta | 89.2 | 35.1 |
| Pe$_2$fo | 7.1 | 2.5 |
| Tripenta | 23.6 | 9.5 |
| Tetrapenta | 7.1 | 2.9 |
| Total yield | 497.6 | 86.2 |

*See Footnote to Example 1

EXAMPLE 8
Production of Pentaerythritol-TMP Ether 272.8 g (2 moles) 22% formaldehyde solution, 268 g (2 moles) TMP, 3200 g (177 moles) water and 96 g (2.4 moles) sodium hydroxide were maintained at 40° C. in a 6-liter reaction vessel. 116 g (2 moles) acrolein (96%) and 1091.2 g (8 moles) 22% formaldehyde solution, previously mixed, were added continuously to this solution over a period of 2 hours at a constant temperature of 40° C. After the addition, the reaction mixture was stirred for another 30 minutes at that temperature and then adjusted to pH 6 with formic acid. The formaldehyde was removed by steam distillation or pressure distillation and the composition of the reaction solution was analyzed by gas chromatography. The residue after evaporation weighed 700 g. The table shows the composition and yields:

| Polyol | Composition of the residue (g) | Yield, based on acrolein (%) |
|---|---|---|
| Pefo | 2.7 | 0.9 |
| Penta | 131.0 | 48.0 |
| TMP | 195.3 | — |
| Dipenta | 19.8 | 7.8 |
| TMP-penta ether | 101.4 | 20.1 |
| TMP-penta formal | 9.0 | 2.4 |
| Tripenta | 2.7 | 1.1 |
| TMP-Penta$_2$ ether | 18.9 | 5.1 |
| Total yield | 480.8 | 85.4 |

Further variations and modifications of the invention will be apparent to those skilled in the art from the foregoing and are intended to be encompassed by the claims appended hereto.

Germany priority application 197 08 695.0 is relied on and incorporated herein by reference.

What is claimed is:

1. A process for producing a polyhydroxy ether having the formula (I)

in which W represents an organic group and OV represents a structural element containing a hydroxyl group, w is the functionality of a multifunctional alcohol having the formula:

m is an integer from 1 to w, and OV is represented by the structured formula (III):

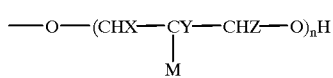  (III)

in which
- X: is H, $C_1$ to $C_6$ alkyl, aryl, alkoxymethyl, or aryloxymethyl;
- Y: is H, $C_1$ to $C_6$ alkyl, aryl, alkoxymethyl, aryloxymethyl, carbalkoxymethyl, carbamidomethyl, or M;
- Z: is H, $C_1$ to $C_6$ alkyl, or aryl, or X-Z taken together is a $C_2$ or $C_3$ alkylene group;
- M: is —$CH_2OH$ or

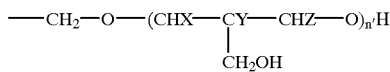

n,n': are integers from 1 to 5; and
in which the alkyl and aryl in X, Y and Z may also be substituted and OV may be the same or different,
comprising reacting the multifunctional alcohol having the formula (II) with an α,β-unsaturated carbonyl compound having the formula

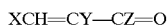  (IV)

in which X, Y and Z have the meanings stated above, except that Y is not M,
with formaldehyde in the presence of an alkali hydroxide or an alkaline earth hydroxide in an aqueous phase at a pH above 7 and a temperature in the range of 0 to 100° C., with the molar ratio of II to IV being 0.05 to 20, the molar ratio of formaldehyde to IV being 2 to 15, and the molar ratio of metal hydroxide equivalent to IV being 1–3, to form a reaction mixture,
acidifying the reaction mixture and optionally isolating reaction products,
wherein the α,β-unsaturated carbonyl compound (IV) and formaldehyde, and optionally the multifunctional alcohol (II) and the alkali hydroxide or alkaline earth hydroxide are added continuously or periodically to an initial aqueous solution or suspension comprising at least 10 mole % of a total amount of the multifunctional alcohol (II) to be used in the reacting step, 10 to 70 mole % of a total amount of the formaldehyde to be used in the reacting step, and at least 10 mole % of a total amount of the alkali hydroxide or alkaline earth hydroxide to be used in the reacting step, and wherein the formaldehyde in the reaction mixture is always in excess with respect to the α,β-unsaturated carbonyl compound (IV).

2. The process according to claim 1 wherein w in formula (II) is an integer from 2 to about 1000.

3. The process according to claim 2 wherein said alcohol is a monomer, oligomer or polymer, and contains primary and/or secondary hydroxyl groups.

4. The process according to claim 2 wherein the organic group W, is aliphatic, olefinic, cycloaliphatic.

5. The process according to claim 4 wherein said alcohol contains at least one member selected from the group consisting of —O—, —COOMe, —COOR, —$SO_3Me$, —$SO_3R$, —$PO_3Me_2$, —$NR_2$, Halogen, CN, —S(O)—, and —$SO_2$—, in which R stands for alkyl and Me stands for an alkali metal or ammonium ion.

6. The process according to claim 1, wherein the multifunctional alcohol (II) is a member selected from the group consisting of α,ω($C_1$–$C_6$—) alkylene glycols, neopentyl glycol, trimethylolethane, trimethylolpropane, pentaerythritol, dipentaerythritol, di-trimethylolethane and di-trimethylolpropane.

7. The process according to claim 1 wherein said multifunctional alcohol is a member selected from the group consisting of difunctional, trifunctional, tetrafunctional, pentafunctional and hexafunctional alcohols.

8. The process according to claim 7 wherein said multifunctional alcohol is selected from the group consisting of ethylene glycol, 1,2-propylene glycol, 1,3-propylene glycol, butane-1,4-diol, hexane-1,6-diol, neopentyl glycol, 2-methyl-1,3-propanediol, 2,2,4-trimethyl-1,3-pentanediol, 1,4-cyclohexanediol, 1,2-cyclohexanediol, tartaric acid, diethanolamine, oxaheptanediol, cyclohexane-1,4-dimethanol, dimethylolacetic acid, glycerol, trimethylolethane, trimethylolpropane, trimethylolacetic acid, diglycerol, pentaerythritol, di-trimethylolethane, 2,6-bis(hydroxymethyl)-2,6-diethyl-4-oxa-1,6-heptanediol, dipentaerythritol, triglycerol, tripentaerythritol, di-tri-trimethylolpropane, tri-trimethylolethane, monosaccharides and disaccharides.

9. The process according to claim 1 wherein the α,β-unsaturated carbonyl compound (IV) is a member selected from the group consisting of acrolein, α-($C_1$–$C_4$)-alkylacrolein, α-arylacrolein, α-alkoxymethylacrolein and α-aryloxymethylacrolein.

10. The process according to claim 1 wherein said α,β-unsaturated carbonyl compound is a ketone.

11. The process according to claim 1 wherein X and Y are H.

12. The process according to claim 1 wherein said α,β-unsaturated compound is an aldehyde selected from the group consisting of acrolein, methacrolein, 2-ethylacrolein, 2-n-propyl-, 2-n-butyl- and 2-isobutylacrolein; 2-phenylacrolein, 2-p-tolylacrolein, 2-p-hydroxyphenylacrolein; 2-methoxymethylacrolein; and 2-phenoxymethylacrolein.

13. The process according to claim 1 wherein 50 to 100 mole % of the total amount of the multifunctional alcohol (II) is provided in the initial aqueous solution or suspension.

14. The process according to claim 1 wherein 50 to 100 mole % of the total amount of the alkali hydroxide or alkaline earth hydroxide is provided in the initial aqueous solution or suspension.

15. The process according to claim 1 wherein 20 to 50 mole % of the total amount of the formaldehyde is provided in the initial aqueous solution or suspension.

16. The process according to claim 1 wherein the multifunctional alcohol (II) is an alcohol having 2 to 6 primary hydroxyl groups and the α,β-unsaturated carbonyl compound (IV) is an aldehyde, and the multifunctional alcohol (II) and the α,β-unsaturated carbonyl compound (IV) are reacted at a molar ratio in the range of from 5 to 0.2.

17. A process according to claim 1 wherein the multifunctional alcohol (II) is an alcohol having 2 to 6 hydroxyl groups, the α,β-unsaturated carbonyl compound (IV) is an aldehyde, and the initial aqueous solution or suspension is an aqueous solution,
wherein 100 mole % of the total amount of the multifunctional alcohol (II), 10 to 30 mole % of the total amount of the formaldehyde, and 100 mole % of the total amount of the alkali or alkaline earth hydroxide are provided in the initial aqueous solution, and wherein the α,β-unsaturated carbonyl compound (IV) and a remaining amount of the formaldehyde are added continuously in parallel or premixed within a period of 0.1 to 5 hours, and wherein the reaction is carried out at 20 to 60° C.

18. The process according to claim 1 wherein, the initial aqueous solution or suspension is an aqueous solution, and wherein the α,β-unsaturated carbonyl compound IV, formaldehyde, multifunctional alcohol and hydroxide are added to said initial aqueous solution.

19. A process for producing a polyhydroxy ether having the formula (I)

$$(HO)_{(w-m)}W(OV)_m \qquad (I)$$

in which W represents an organic group and OV represents a structural element containing a hydroxyl group, w is the functionality of a multifunctional alcohol selected from the group consisting of polyvinyl alcohol, starch, polysaccharides, poly(meth)acrylates and copolymers, containing as a monomeric unit, a hydroxyalkyl (meth)acrylate, with the proviso that w is an integer from 2 to about 1000, m is an integer from 1 to w, and OV is represented by the structural formula (III):

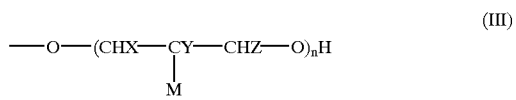
$$—O—(CHX—CY—CHZ—O)_nH \atop \quad\quad\quad\quad\;\; | \atop \quad\quad\quad\quad\; M \qquad (III)$$

in which

X: is H, $C_1$ to $C_6$ alkyl, aryl, alkoxymethyl, or aryloxymethyl;

Y: is H, $C_1$ to $C_6$ alkyl, aryl, alkoxymethyl, aryloxymethyl, carbalkoxymethyl, carbamidomethyl, or M;

Z: is H, $C_1$ to $C_6$ alkyl, or aryl, or X-Z taken together is a $C_2$ or $C_3$ alkylene group;

M: is —$CH_2OH$ or

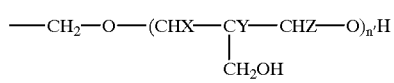
$$—CH_2—O—(CHX—CY—CHZ—O)_{n'}H \atop \quad\quad\quad\quad\quad\quad\; | \atop \quad\quad\quad\quad\quad\; CH_2OH$$

n,n': are integers from 1 to 5; and in which the alkyl and aryl in X, Y and Z may also be substituted and OV may be the same or different, comprising reacting the multifunctional alcohol with an α,β-unsaturated carbonyl compound having the formula

$$XCH=CY—CZ=O \qquad (IV)$$

in which X, Y and Z have the meanings stated above, except that Y is not M, with formaldehyde in the presence of an alkali hydroxide or an alkaline earth hydroxide in an aqueous phase at a pH above 7 and a temperature in the range of 0 to 100° C., with the molar ratio of the multifunctional alcohol to the α,β-unsaturated carbonyl compound IV being 0.05 to 20, the molar ratio of formaldehyde to the α,β-unsaturated carbonyl compound IV being 2 to 15, and the molar ratio of metal hydroxide equivalent to the α,β-unsaturated carbonyl compound IV being 1–3, to form a reaction mixture, acidifying the reaction mixture and optionally isolating reaction products, wherein the α,β-unsaturated carbonyl compound (IV) and formaldehyde, and optionally the multifunctional alcohol and the alkali hydroxide or alkaline earth hydroxide are added continuously or periodically to an initial aqueous solution or suspension comprising at least 10 mole % of a total amount of the multifunctional alcohol to be used in the reacting step, 10 to 70 mole % of a total amount of the formaldehyde to be used in the reacting step, and at least 10 mole % of a total amount of the alkali hydroxide or alkaline earth hydroxide to be used in the reacting step, and wherein the formaldehyde in the reaction mixture is always in excess with respect to the α,β-unsaturated carbonyl compound (IV).

20. A process for producing a polyhydroxy ether having the formula (I)

$$(HO)_{(w-m)}W(OV)_m \qquad (I)$$

in which W represents an organic group and OV represents a structural element containing a hydroxyl group, w is the functionality of a multifunctional alcohol having the formula:

$$W(OH)_w \qquad (II),$$

m is an integer from 1 to w, and OV is represented by the structural formula (III):

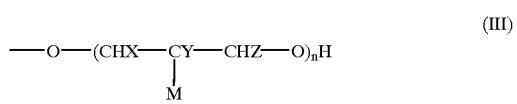
$$—O—(CHX—CY—CHZ—O)_nH \atop \quad\quad\quad\quad\;\; | \atop \quad\quad\quad\quad\; M \qquad (III)$$

in which

X: is H, $C_1$ to $C_6$ alkyl, aryl, alkoxymethyl, or aryloxymethyl;

Y: is H, $C_1$ to $C_6$ alkyl, aryl, alkoxymethyl, aryloxymethyl, carbalkoxymethyl, carbamidomethyl, or M;

Z: is H, $C_1$ to $C_6$ alkyl, or aryl, or X-Z taken together is a $C_2$ or $C_3$ alkylene group;

M: is —$CH_2OH$ or

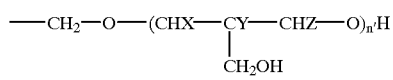
$$—CH_2—O—(CHX—CY—CHZ—O)_{n'}H \atop \quad\quad\quad\quad\quad\quad\; | \atop \quad\quad\quad\quad\quad\; CH_2OH$$

n,n': are integers from 1 to 5; and in which the alkyl and aryl in X, Y, and Z also may be substituted and OV may be the same or different, comprising reacting the multifunctional alcohol having the formula (II) with an α,β-unsaturated carbonyl compound having the formula

$$XCH=CY—CZ=O \qquad (IV)$$

in which X, Y and Z have the meanings stated above, except that Y is not M, and in which the alkyl and aryl groups in X and Y in formula IV have a substituent selected from the group consisting of —N-alkyl$_2$, —N-aryl$_2$, —OC(O)alkyl, —OC(O)aryl, —COO-alkyl, —COO-aryl, and —CON-alkyl$_2$, with formaldehyde in the presence of an alkali hydroxide or an alkaline earth hydroxide in an aqueous phase at a pH above 7 and a temperature in the range of 0 to 100° C., with the molar ratio of II to IV being 0.05 to 20, the molar ratio of formaldehyde to IV being 2 to 15, and the molar ratio of metal hydroxide equivalent to IV being 1–3, to form a reaction mixture, acidifying the reaction mixture and optionally isolating reaction products, wherein the α,β-unsaturated carbonyl compound (IV) and formaldehyde, and optionally the multifunctional alcohol (II) and the alkali hydroxide or alkaline earth hydroxide are added continuously or periodically to an initial aqueous solution or suspension comprising at least 10 mole % of a total amount of the multifunctional alcohol (II) to be used in the reacting step, 10 to 70 mole % of a total amount of the formaldehyde to be used in the reacting step, and at least 10 mole % of a total amount of the alkali hydroxide or alkaline earth hydroxide to be used in the reacting step, and wherein the formaldehyde in the reaction mixture is always in excess with respect to the α,β-unsaturated carbonyl compound (IV).

21. A process for producing a polyhydroxy ether having the formula (I)

$$(HO)_{(w-m)}W(OV)_m \qquad (I)$$

in which W represents an organic group and OV represents a structural element containing a hydroxyl group, w is the functionality of a multifunctional alcohol having the formula:

$$W(OH)_w \qquad (II),$$

m is an integer from 1 to w, and OV is represented by the structural formula (III):

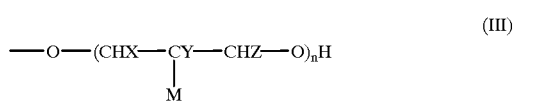

in which

X: is H, $C_1$ to $C_6$ alkyl, aryl, alkoxymethyl, or aryloxymethyl;

Y: is H, $C_1$ to $C_6$ alkyl, aryl, alkoxymethyl, aryloxymethyl, carbalkoxymethyl, carbamidomethyl, or M;

Z: is H, $C_1$ to $C_6$ alkyl, or aryl, or X-Z taken together is a $C_2$ or $C_3$ alkylene group;

M: is —$CH_2OH$ or

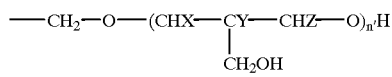

n,n': are integers from 1 to 5; and in which the alkyl and aryl in X, Y and Z may also be substituted and OV may be the same or different, comprising reacting the multifunctional alcohol having the formula (II) with an α,β-unsaturated carbonyl compound having the formula $$XCH=CY-CZ=O \qquad (IV)$$

in which X, Y and Z have the meanings stated above, except that Y is not M, and with the proviso that said α,β-unsaturated carbonyl compound is a ketone selected from the group consisting of vinyl-alkyl ketones and vinyl-aryl ketones, with formaldehyde in the presence of an alkali hydroxide or an alkaline earth hydroxide in an aqueous phase at a pH above 7 and a temperature in the range of 0 to 100° C., with the molar ratio of II to IV being 0.05 to 20, the molar ratio of formaldehyde to IV being 2 to 15, and the molar ratio of metal hydroxide equivalent to IV being 1–3, to form a reaction mixture, acidifying the reaction mixture and optionally isolating reaction products, wherein the α,β-unsaturated carbonyl compound (IV) and formaldehyde, and optionally the multifunctional alcohol (II) and the alkali hydroxide or alkaline earth hydroxide are added continuously or periodically to an initial aqueous solution or suspension comprising at least 10 mole % of a total amount of the multifunctional alcohol (II) to be used in the reacting step, 10 to 70 mole % of a total amount of the formaldehyde to be used in the reacting step, and at least 10 mole % of a total amount of the alkali hydroxide or alkaline earth hydroxide to be used in the reacting step, and wherein the formaldehyde in the reaction mixture is always in excess with respect to the α,β-unsaturated carbonyl compound (IV).

* * * * *